(12) United States Patent
Woias et al.

(10) Patent No.: US 11,571,529 B2
(45) Date of Patent: Feb. 7, 2023

(54) ARRANGEMENT AND BASE PART FOR AN INHALER, AND AN INHALER

(71) Applicant: KÖRBER TECHNOLOGIES GMBH, Hamburg (DE)

(72) Inventors: Peter Woias, Freiburg (DE); Frank Goldschmidtboeing, Ortenberg (DE); Uwe Pelz, Schallstadt (DE); Muhannad Ghanam, Freiburg (DE); Jan Jaklin, Freiburg (DE); Sonali Rath, Heilsbronn (DE)

(73) Assignee: KÖRBER TECHNOLOGIES GMBH, Hamburg (DE)

( * ) Notice: Subject to any disclaimer, the term of this patent is extended or adjusted under 35 U.S.C. 154(b) by 870 days.

(21) Appl. No.: 16/422,216

(22) Filed: May 24, 2019

(65) Prior Publication Data

US 2019/0358416 A1    Nov. 28, 2019

(30) Foreign Application Priority Data

May 28, 2018 (DE) .......................... 102018112699.9
Nov. 8, 2018 (DE) .......................... 102018127927.2

(51) Int. Cl.
*A61M 11/00* (2006.01)
*A61M 15/06* (2006.01)
(Continued)

(52) U.S. Cl.
CPC ............. *A61M 15/06* (2013.01); *A24F 40/46* (2020.01); *A24F 40/485* (2020.01); *A24F 40/51* (2020.01);
(Continued)

(58) Field of Classification Search
CPC ................ A61M 15/06; A61M 11/042; A61M 2205/8206; A24F 40/458; A24F 40/46; A24F 40/51; A24F 40/10; A24F 40/60
(Continued)

(56) References Cited

U.S. PATENT DOCUMENTS

2014/0216485 A1    8/2014  Egoyants et al.
2014/0345633 A1    11/2014  Talon et al.
(Continued)

FOREIGN PATENT DOCUMENTS

DE    10 2009 029 768 B4    2/2013
DE    10 2016 120 803 A1    5/2018
(Continued)

OTHER PUBLICATIONS

European Search Report issued by the European Patent Office dated Feb. 5, 2020 for parallel European Patent Application No. 19 176 138.6.
(Continued)

*Primary Examiner* — Khiem M Nguyen
(74) *Attorney, Agent, or Firm* — Saliwanchik, Lloyd & Eisenschenk

(57) ABSTRACT

An arrangement for an inhaler comprises at least one electric evaporator for evaporating liquid supplied from the evaporator, and for adding the evaporated liquid to an air flow flowing through the inhaler to form an aerosol, and a flow rate measuring arrangement for measuring the volume and/or mass flow of the air flow flowing through the inhaler. The flow rate measuring arrangement comprises a heating device, a downstream temperature sensor arranged downstream of the heating device for measuring an air outlet temperature and an electronic control device, wherein the electronic control device is adapted to determine the volume and/or mass flow of the air flow flowing through the inhaler
(Continued)

on the basis of a temperature difference between the air outlet temperature and an air inlet temperature of the air flow upstream of the heating device.

25 Claims, 4 Drawing Sheets

(51) Int. Cl.
| | | |
|---|---|---|
| *A24F 40/46* | (2020.01) | |
| *A24F 40/485* | (2020.01) | |
| *A24F 40/51* | (2020.01) | |
| *A61M 11/04* | (2006.01) | |
| *A24F 40/10* | (2020.01) | |
| *A24F 40/60* | (2020.01) | |

(52) U.S. Cl.
CPC ............... *A24F 40/10* (2020.01); *A24F 40/60* (2020.01); *A61M 11/042* (2014.02); *A61M 2205/8206* (2013.01)

(58) Field of Classification Search
USPC .................................................. 128/200.21
See application file for complete search history.

(56) References Cited

U.S. PATENT DOCUMENTS

| | | |
|---|---|---|
| 2016/0360786 A1 | 12/2016 | Bellinger et al. |
| 2016/0366939 A1 | 12/2016 | Alarcon et al. |
| 2018/0132523 A1 | 5/2018 | Biel et al. |
| 2019/0246696 A1 | 8/2019 | Schmidt et al. |
| 2019/0328039 A1 | 10/2019 | Romming et al. |

FOREIGN PATENT DOCUMENTS

| | | |
|---|---|---|
| EP | 2 563172 B1 | 3/2017 |
| EP | 3 560 363 A1 | 10/2019 |
| WO | WO 2018/029077 A1 | 2/2018 |

OTHER PUBLICATIONS

First Examination Report issued by the German Patent and Trademark Office dated Aug. 5, 2021 for the German Priority Application No. 10 2018 127 927.2.

ARRANGEMENT AND BASE PART FOR AN INHALER, AND AN INHALER

CROSS REFERENCE TO A RELATED APPLICATION

This application claims priority under 35 U.S.C. § 119(e) of German Patent Application No. DE 10 2018 112699.9, filed May 28, 2018 and German Patent Application No. DE 10 2018 127927.2, filed Nov. 8, 2018; both of which are incorporated herein by reference in their entirety.

FIELD OF THE INVENTION

The present invention relates to an arrangement for an inhaler comprising at least one electric evaporator for evaporating liquid supplied to the evaporator and for adding the evaporated liquid to an air stream flowing through the inhaler to form an aerosol, and to a flow rate measuring arrangement for measuring the volume and/or mass flow of the air stream flowing through the inhaler. The present invention also relates to a base part for an inhaler and to an inhaler.

BACKGROUND OF THE INVENTION

A large number of inhalers or electronic cigarette products having such an arrangement are known in the art.

Common inhalers, for example electronic cigarette products, are activated by a vacuum switch, for example. As soon as the user creates a negative pressure relative to the ambient pressure by drawing at a mouth end of the inhaler, the evaporation of the liquid is activated and is added to the air stream as aerosol or vapour. The liquid comprises flavouring substances and/or active ingredients, in particular nicotine, which are administered to the user with the aerosol or vapour. If the negative pressure falls below a switching threshold, the evaporation is stopped. The evaporation process is thus independent of the intensity of the generated negative pressure as long as the switching threshold is exceeded or not reached.

However, the consumer of a conventional cigarette expects a different behaviour. In the case of a conventional cigarette, the strength of the draw can be used to control the combustion of the tobacco and/or tobacco product and thus the absorption of smoke. Such a possibility would also be desirable for an electronic cigarette product or an inhaler.

In order to consider the strength of the consumer's draw, prior art inhalers have flow rate measuring devices for measuring the volume and/or mass flow of the air flowing through the inhaler, see, for example, DE 10 2009 029 768 B4. The disadvantage of the known measuring arrangements is the restriction of the measuring ranges. The vacuum switches only operate reliably at comparatively high vacuum levels, while the flow rate measuring arrangements primarily operate reliably at comparatively low vacuum levels, pressure differentials or flow velocities. Furthermore, known mechanical elements such as rotating vane anemometers, see, for example, EP 2 563 172 B1, are complex, expensive and susceptible to contamination and are only conditionally suitable for recording absolute measurement values, for example for switching on the inhaler.

BRIEF SUMMARY OF THE INVENTION

The object of the invention is to provide an arrangement for an inhaler that allows improved and reliable flow measurement.

The invention solves this problem with the features of the independent claims.

In accordance with the invention, it is suggested that the flow rate measuring arrangement comprises a heating device, a temperature sensor for measuring an air outlet temperature arranged downstream of the heating device and an electronic control device, said electronic control device being adapted to determine the volume and/or mass flow of the air flowing through the inhaler on the basis of a temperature difference between the air outlet temperature and an air inlet temperature of the air flow upstream of the heating device.

The arrangement according to the invention allows an exact flow measurement on a thermal basis. The air inlet temperature is a temperature upstream of the heating device and corresponds, for example, to the ambient temperature. The heating device is arranged to heat air to the air outlet temperature, wherein the heated air is fed to the downstream temperature sensor arranged downstream of the heating device. The heating device and/or the temperature sensor can, for example, comprise an ohmic resistor and/or a thermistor, for example a hot or cold conductor.

The arrangement according to the invention is free of mechanical parts which have to be moved for said flow measurement and is therefore less susceptible to contamination.

The heat transported by the air from the heating element to the temperature sensor arranged downstream provides insight into the mass and/or volume flow that is transported with the air. On the basis of the mass and/or volume flow, the flow velocity, the draw strength or the suction pressure can be inferred.

Preferably, the flow rate measuring arrangement comprises an upstream temperature sensor arranged upstream of the heating device for measuring the air inlet temperature of the air flow in order to determine an exact reference value for the air inlet temperature and to be able to advantageously determine the temperature difference. The arrangement of at least two temperature sensors, wherein in particular one of the temperature sensors is arranged upstream of the heating device and one of the temperature sensors is arranged downstream of the heating device, allows any arrangement of the flow rate measuring arrangement within the inhaler. The arrangement of the flow rate measuring arrangement downstream of the evaporator is also conceivable, since the temperature difference can be measured in an accurate and reliable way.

In other embodiments, the upstream temperature sensor can be dispensed with, wherein the air inlet temperature can be estimated or otherwise be made available, for example via the local weather forecast, the Internet and/or information technology devices connected to the inhaler.

It is advantageous to place the heating device upstream of the evaporator(s) of the inhaler in order to be able to measure a temperature with the temperature sensor(s) in air without added liquid. This allows the advantageous determination of the volume and/or mass flow due to the known heat capacity of air.

The heating device is preferably formed by one of the evaporators in order to be able to ensure an effective assembly of the flow rate measuring arrangement with only a few components.

The invention further provides an arrangement comprising at least one electric evaporator for evaporating liquid supplied to the evaporator and for adding the evaporated liquid to a stream of air flowing through the inhaler to form an aerosol, wherein the arrangement comprises, in accordance with the invention, a reheating device for reheating the aerosol to achieve a higher vapour quality.

The reheating device is advantageously located downstream of the evaporator and/or in relation to the evaporator, i.e. the aerosol is reheatable or can be kept warm, after being generated by means of evaporation of the liquid at the evaporator via the reheating device. After evaporation of the liquid, the aerosol or the vapour or the air flow with the added liquid is heated by the evaporator with the reheating device. Thus, condensation can be avoided and flavouring substances and/or active ingredients, such as nicotine, can be reliably transported by the air flow in the aerosol or vapour.

The droplet size can be influenced by said reheating and said efficacy of the flavouring substances and/or active ingredients can be optimised. Said reheating of the air stream or the aerosol preferably leads to the air becoming pleasantly warm for the consumer and already condensed droplets of the aerosol evaporating and/or further condensation being prevented. The steam delivered to the consumer is therefore finer and has a higher steam quality.

The heating device can be advantageously formed by the reheating device.

Preferably the electronic control device is arranged to determine the volume and/or mass flow of the air flowing through the inhaler by applying the equation $\Delta m/\Delta t = P/(c \cdot \Delta T)$, wherein $\Delta m/\Delta t$ is the mass flow, P is the heating power of the heating device, $\Delta T$ is the temperature difference between the air outlet temperature and the air inlet temperature and c is the known or estimated heat capacity of the air heated by the heating device (with or without aerosol, depending on the arrangement of the heating device) to allow easy and accurate determination of the mass flow.

The arrangement preferably comprises a wattmeter to determine the heating power P of the heating device in order to be able to measure the heating power over a time interval and thus to determine the heat supplied to the air and/or the aerosol or steam.

The electronic control device for controlling at least one evaporator as a function of the measured flow rate of the air flowing through the inhaler is advantageous in order to make it possible for the consumer to evaporate liquid and/or to add flavouring substances and/or active ingredients to the air flow in accordance with the draw or suction pressure applied.

The evaporator can preferably be controlled on the basis of a signal from an actuating member in order to allow the consumer to individually adjust the evaporation of liquid and/or the addition of flavouring substances and/or active ingredients to the air flow. The actuating member may comprise, for example, a mouth pressure sensor, a finger pressure gauge, switch and/or button. In particular, an electronic and/or capacitive actuating member may be provided at the mouth end and/or at a tube extending between the mouth end and a distal end of the inhaler.

In an advantageous embodiment, at least the heating device and the downstream temperature sensor are arranged in a measuring duct in order to allow flow measurement independent of the evaporation of the liquid. The measuring duct can be provided separate at least in part from the air duct or main air duct in which the liquid is added as an aerosol, for example as a bypass. The measuring duct can be formed in one embodiment by the air duct or a portion of the air duct upstream of the evaporator.

An advantage of the at least one electric evaporator is a multi-duct, in particular temperature-controlled evaporator, in order to make possible an improved and easily adjustable and/or controllable administration of flavouring substances and/or active ingredients. A multi-duct evaporator can, for example, be formed by an evaporator unit having a plurality of evaporators and/or at least one evaporator having a plurality of separately controllable, heatable and/or activatable regions.

The evaporation quantity of the evaporated liquid, the nicotine quantity of the evaporated liquid, the temperature of the evaporator, the duty cycle of the evaporator and/or the number of activated evaporators and/or evaporator regions adjustable, controllable and/or regulatable are advantageous in order to be able to provide a high aerosol or steam quality.

The evaporation quantity, the nicotine quantity, the temperature, the duty cycle and/or the number of activated evaporators and/or evaporator regions may be adjustable by the consumer and/or electronically. The evaporation quantity, the nicotine quantity, the temperature, the duty cycle and/or the number of activated evaporators and/or evaporator regions may for example be adjustable depending on the composition of the liquid and/or the consumer's consumption habits. In particular and preferably over the duration of an evaporation interval, the temperature and/or the duty cycle is temporarily increasing, temporarily decreasing and/or temporarily constant.

The evaporation quantity, the nicotine quantity, the temperature, the duty cycle and/or the number of activated evaporators and/or evaporator regions are preferably variable independently of one another, allowing, for example, a concentration of flavouring substances and/or active ingredients independent of vapour quantity.

The arrangement preferably has a force sensor for measuring the finger pressure or the mouth pressure applied by the consumer in order to allow easy adjustment of the inhaler by the consumer. For example, a force sensor for measuring the finger pressure is provided on a housing of the inhaler and/or a mouth force sensor for measuring the mouth pressure is provided on the mouth end of the inhaler. The force sensor preferably provides a signal for setting the inhaler, in particular the evaporator, and thus allows activation, control and/or regulation of flavouring substances and/or administration of active ingredients.

Preferably, the flow rate measuring arrangement is usable as an input member for the input of information into the electronic control device by the consumer to allow intuitive control and/or regulation of the inhaler.

An advantage is the flow rate measuring arrangement for detecting blowing or drawing air into the inhaler by the consumer as an input, in particular to encode atypical breathing patterns, for example an atypical breathing rate and/or an atypical breathing volume, as an input for inhalation.

Preferably, the flow rate measuring arrangement is useful for activating the inhaler to avoid unintentional activation of the inhaler. For example, this embodiment can be designed without an on/off switch or something similar on the outside of the inhaler housing.

The flow rate measuring arrangement is preferably used by the consumer to adjust the steam quantity, for example to adapt the steam quantity to the draw strength of the consumer and to make possible a smoking experience similar to that of a conventional cigarette.

In a preferred embodiment, an orifice and/or bypass duct is provided to regulate the flow conditions of at least one evaporator to make possible an improved steam quality and/or flow measurement.

In a preferred embodiment, the evaporator is at least silicon-based at least in part, and is preferably a microelectro-mechanical system (MEMS), to be able to provide an effective and reliable evaporator.

BRIEF DESCRIPTION OF THE FIGURES

Hereafter, the invention is described by means of preferred embodiments and referring to the attached drawings.

DETAILED DESCRIPTION

Figure 1:
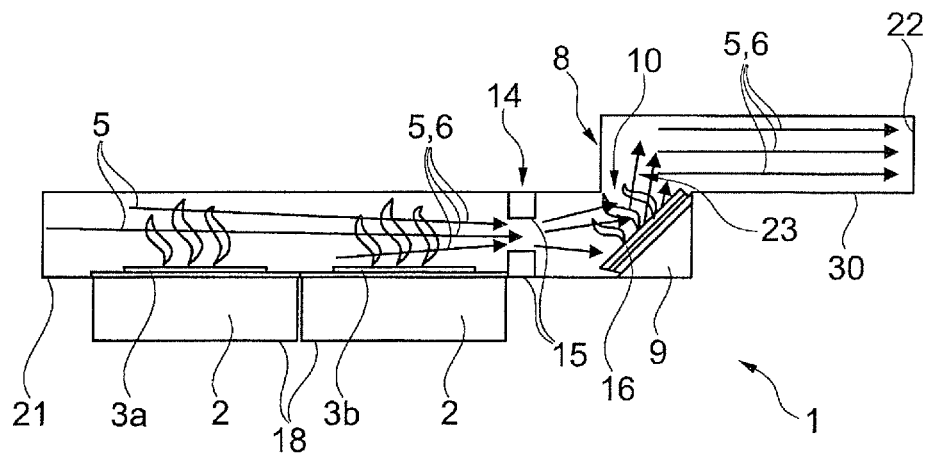
FIG. 1 is a section through an arrangement having a reheating device.

FIG. 1 shows an arrangement 1 having a reheating device 10. The arrangement 1 is provided for an inhaler 27 shown in FIG. 4. The consumer applies a vacuum to the arrangement 1 by drawing at a mouth end 32 of the inhaler 27. The vacuum causes air to enter arrangement 1 at an inlet end 21 of the arrangement 1 and the vacuum causes air to flow 5 through the arrangement 1 from the inlet end 21 to an outlet end 22, see FIG. 1.

The arrangement 1 comprises in this example two evaporators 3a, 3b to evaporate a liquid 2 comprising flavouring substances and/or active ingredients. Evaporation adds aerosol 6 or vapour containing the flavouring substances or active ingredients to the air flow 5. The aerosol 6 transports the flavouring substances and/or active ingredients comprised by the liquid 2 in the air flow 5 to the outlet end 22 associated with the mouth end 32. In the embodiment shown, an air duct 30 extends between the inlet end 21 and the outlet end 22, through which air duct the air flow 5 is guided. The air flow 5 advantageously transports the aerosol 6 through the air duct 30. The mass flow $\Delta m/\Delta t$ is the air mass or air/aerosol mass $\Delta m$, which flows through the air duct 30 within a time interval $\Delta t$. The (air) mass flow influences the smoking experience or the administration of flavouring substances and/or active substances contained in aerosol 6.

Said evaporators 3a, 3b are, for example, connected to an electronic control device 29 provided in the inhaler 27 and/or an energy storage device 26 provided in the inhaler 27 for the supply of energy. For evaporation and/or heat generation, said evaporators 3a, 3b advantageously obtain an output P over a defined and/or definable period of time. Said evaporators 3a, 3b advantageously cause the temperature of the air flow 5 downstream of each evaporator 3a, 3b to be higher than upstream of the respective evaporator 3a, 3b, i.e. said evaporators 3a, 3b cause a temperature difference $\Delta T$ in the air flow 5.

Said evaporators 3a, 3b are sequentially arranged and at a distance from each other along the air flow 5 or in the air duct 30 in the direction of flow, i.e. said evaporators 3a, 3b are sequentially connected in the direction of the air flow 5. Said evaporators 3a, 3b can be adapted to evaporate different liquids 2 and/or liquid 2 at different temperatures.

Figure 5:
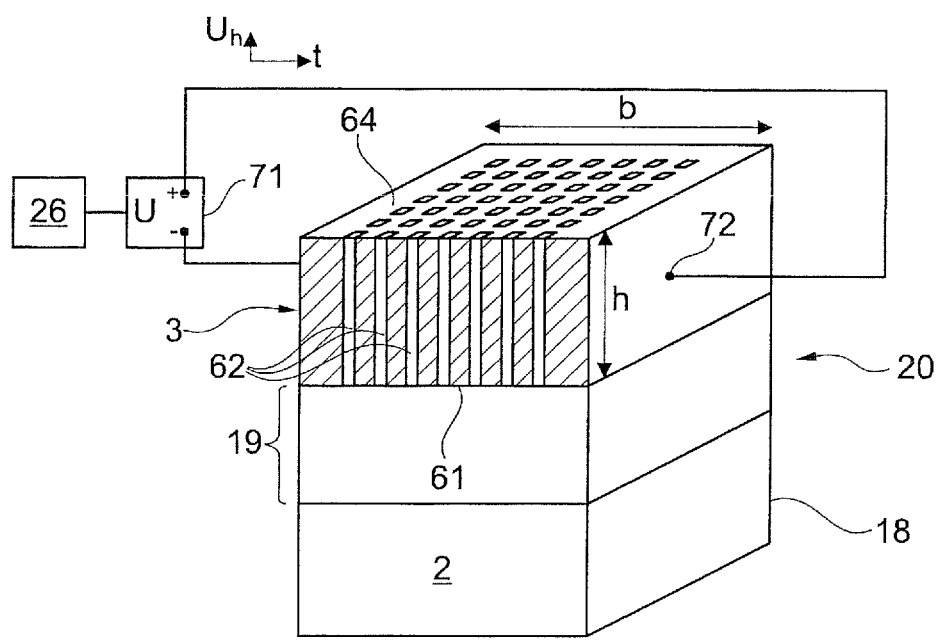
FIG. 5 is a perspective cross-sectional view of an evaporator unit having a liquid reservoir.

Said liquid 2 is stored in one or more, herein two exemplary liquid reservoirs 18, and can be supplied to the respective evaporator 3a, 3b by means of a wick structure 19 shown in FIG. 5 between the respective evaporator 3a, 3b and the corresponding liquid reservoir 18. In an embodiment (not shown), the arrangement 1 may comprise an evaporator 3a, 3b and/or a liquid reservoir 18.

In the embodiment shown in FIG. 1, the evaporators 3a, 3b are followed by a choke valve 14, i.e. said choke valve 14 is located downstream of the evaporators 3a, 3b. Said choke valve 14 is a narrowing of the cross section of the volume available to the air flow 5. Said choke valve 14 thus advantageously causes a setting of the draw resistance, the mass flow $\Delta m/\Delta t$ of the air flow 5 through the air duct 30 and/or turbulence of the air flow 5. The turbulence of the air flow 5 can be specifically used to influence the heat transport within the air flow 5 and/or to mix the air flow 5, to cause a turbulent flow or to suppress a laminar flow. The improved heat transfer within the air flow due to said choke valve 14 can preferably reduce the recondensation of the aerosol 6 and/or the steam.

Said choke valve 14 is advantageously arranged to reduce the cross section of the air duct 30. The change in the cross section caused by said choke valve 14 is preferably adjustable. On the outside of the inhaler 27, an adjusting device accessible to consumers may be for example provided to adjust the cross section of the choke valve 14. The adjusting device may include, for example, a setting wheel, switch, pushbutton and/or the like.

The choke valve 14 and/or the draw resistance can be adjusted in an embodiment by the consumer by blowing or breathing out and/or sucking or drawing. A particular sequence of blowing and/or drawing may encode a corresponding draw resistance and/or an adjustment of the choke valve 14. The adjustment of the choke valve 14 may be displayable on a display device 102 provided on the outside of the inhaler 27.

Preferably, the cross section of the choke valve 14 is preferably electrically or electronically adjustable. Said choke valve 14 may, for example, have one or more piezoelectric or inductively controlled elements 15 which are adapted to adjust the cross section of the choke valve 14 on the basis of electrical signals.

The piezoelectric and/or inductive element 15 is or are arranged in such a way that the cross section of the air duct 30 or the volume available to the air flow 5 can be advantageously changed due to the electric signals or the absence thereof. A piezoelectric or inductive element 15 can for example transversely to the direction of flow or circumferentially surround the air flow 5. In another embodiment, a plurality of piezoelectric and/or inductive elements 15 can be arranged at the same height in the direction of flow in order to achieve a narrowing of the cross section.

Said choke valve 14 is for example connected to the electronic control device 29 provided in the inhaler 27 to adjust the cross section of the choke valve 14.

In another embodiment, the inhaler has a plurality of air ducts 30. Each of the air ducts 30 may have an associated choke valve 14, advantageously each choke valve 14 being fully closable to suppress the air flow 5 through the respective air duct 30. Each of the air ducts is preferably individually activatable or switchable to allow or suppress the air flow 5 through the respective air duct 30. Suppressing the air flow 5 through one or more of said air ducts 30 and guiding the air flow 5 through one or more of the air ducts 30 causes reliable regulation of the draw resistance, the mass flow and the addition of flavouring substances and/or active ingredients to the total air flow, which is for example composed of the sum of all air flows 5 through passable or activated ducts.

In the embodiment shown in FIG. 1, a reheating device 10 is arranged downstream of the choke valve 14. In this example, said choke valve 14 is arranged in the direction of the flow between the evaporators 3*a*, 3*b* and the reheating device 10. An air flow 5 in which turbulence has advantageously been created by the choke valve 14 hits the reheating device 10 and allows effective heating of the air flow 5.

The reheating device 10 advantageously comprises a heating element 16 adapted to heat up the air stream 5 containing aerosol 6 or steam, hitting the reheating device 10. The reheating device 10 is advantageously different from the evaporator 3. Only via the air flow 5 as aerosol 6 and/or steam may the reheating device 10 be advantageously supplied with liquid 2.

For the supply of energy, the heating element 16, for example, is connected to the electronic control device 29 provided in the inhaler 27 and/or the energy storage device 26 provided in the inhaler 27. For heat generation, advantageously, the heating element 16 utilises a power P over a defined or definable period of time. The heating element 16 causes the temperature of the air flow 5 downstream of the heating element 16 to be higher than upstream of the heating element, i.e. the heating element 16 causes a temperature difference ΔT in the air flow 5. The air flow 5 temperature increase by means of the heating element 16 or by the reheating device 10, advantageously counteracts recondensation of the aerosol 6 transported in the air flow 5 or a precipitation thereof at the air duct 30 and/or at other components of the inhaler.

The arrangement 1 in FIG. 1 advantageously comprises air guide elements 23 which are adapted to guide and/or to create turbulence in the air flow 5. In this embodiment, the air guide elements 23 comprise a deflection 8 of the air flow 5 or the air duct 30 and an air guide device 9, which is for example designed as an inclination or beveling to the direction of flow of the reheating device 10 or the heating element 16. The air guide device 9 associated with the reheating device 10 causes the air flow 5 to hit the reheating device 10 at an angle between 10° and 80°, advantageously between 20° and 70°, preferably between 30° and 60°, particularly preferably between 40° and 50°, for example of 45°, thus enabling the reheating device 10 to effectively heat up the air flow 5.

Advantageously, the heating temperature of the evaporator 3 and/or the reheating device 10 is adjustable, controllable and/or regulatable taking into account the different vapour phases of the components of said liquid 2 or said aerosol 6. In the case of a pulsed control or heating of the evaporator 3 and/or the reheating device 10, an adjustment of the duty cycle to the defined power or heat output is provided. Advantageously, the temperature change ΔT and/or the output P caused by the evaporator 3 and/or the reheating device 10 is adjustable to enable a high quality of the composition of the aerosol 6.

FIG. 2 shows an arrangement 1 having a plurality of reheating devices 10 sequentially arranged in the direction of flow. The embodiment shown is explained by means of the differences to the embodiment in FIG. 1. The reheating devices 10 comprise at least one heating element 16*a*, 16*b*, 16*c* each. The heating elements 16*a*, 16*b*, 16*c* are sequentially arranged in the direction of the flow and are spaced apart from each other. Each of the heating elements 16*a*, 16*b*, 16*c* heats up the air flow with a power Pi, said power Pi being unique for each of the heating elements 16*a*, 16*b*, 16*c*, and being in particular uniquely adjustable for each heating element 16*a*, 16*b*, 16*c*, rising and/or falling in the direction of the flow.

One of the heating elements 16*a* is arranged opposite the first evaporator 3*a* in the direction of the flow, i.e. the heating element 16*a* is at least partially facing the evaporator 3*a* and is arranged transversely to the direction of the flow on the opposite side in the air duct 30. A second evaporator 3*b* is arranged downstream of the first evaporator 3*a*, opposite which a further one of the heating elements 16*b* is arranged. Downstream of the evaporators 3*a*, 3*b* and the choke valve 14, another one of the heating elements 16*c* is arranged. The reheating devices 10 and the heating elements 16*a*, 16*b*, 16*c* are arranged sequentially in the direction of the flow and each of the reheating devices 10 is arranged to increase the temperature of the air flow 5 by a temperature difference ΔT, wherein said temperature difference ΔT may be unique for each of the reheating devices 10, in particular uniquely adjustable for each of the reheating devices 10, increasing downstream and/or decreasing downstream.

The evaporated liquid 2 and the air contained in the air flow 5 expands when evaporated by the evaporator 3*a*, 3*b* in accordance with the heat supplied by the evaporator 3*a*, 3*b* and/or by the evaporation or formation of the aerosol. This causes said aerosol 6 to spread in the air duct 30, in particular perpendicular to the direction of the flow between the inlet end 21 and the outlet end 22. The reheating device 10 opposite one of the evaporators 3*a*, 3*b* or the heating element 16*a*, 16*b* opposite one of the evaporators 3*a*, 3*b* is arranged in such a way that the wall of the air duct 30 is heated opposite the evaporators 3*a*, 3*b* in order to suppress a precipitation or condensation of the aerosol 6.

The reheating devices 10 or the heating elements 16*a*, 16*b*, 16*c* are spaced apart and/or arranged sequentially in the direction of the flow. Between the reheating devices 10 and/or the evaporators 3*a*, 3*b* the air flow 5 is not heated up and cools down. The reheating devices 10 or the heating elements 16*a*, 16*b*, 16*c* are adapted to heat up the air flow 5 in each case with a power Pi over a period of time. The power Pi of the reheating devices 10 or of the heating elements 16*a*, 16*b*, 16*c* is adjustable and/or can be the same or vary, in particular increasing or decreasing in the direction of flow.

FIG. 3 shows an arrangement 1 with the heat conducting elements 11*a*, 11*b* surrounding the air flow 5. The air flow 5 extends through the preferably annular heat conducting elements 11*a*, 11*b*. In this embodiment, two heat conducting elements 11*a*, 11*b* are spaced apart in the direction of the flow. In other embodiments, one or more than two annular heat conducting elements 11*a*, 11*b* may be provided.

The heat conducting elements 11*a*, 11*b* are advantageously heatable by one of the evaporators 3*a*, 3*b*. Each heat conducting element 11*a*, 11*b* is advantageously heatable by at least one of the evaporators 3*a*, 3*b*. For example, the first heat conducting element 11*a* in the direction of the flow is heatable by the first evaporator 3*a* in the direction of the flow and/or the second heat conducting element 11*b* arranged downstream of the first heat conducting element 11*a* is heatable by the second evaporator 3*b* arranged downstream of the first evaporator 3*a*. The heat emitted by one of the evaporators 3*a*, 3*b* to the respective heat conducting element 11*a*, 11*b* is used in this case in order to avoid condensation of the aerosol 6 and to heat up the air flow 5, for example in a cylindrical portion of the air duct 30, such as a main air duct of the inhaler 27.

In this embodiment, the evaporators 3*a*, 3*b* are embedded in the respective heat conducting elements 11*a*, 11*b*, i.e. the heat conducting elements 11*a*, 11*b* each preferably have a receptacle on or in which the respective evaporator 3a, 3b can be accommodated. The receptacle can, for example, be a recess.

Cooling elements 13 or cooling lines can be provided between the heat conducting elements 11a, 11b. The cooling elements 13 can be adapted for passive cooling of the aerosol 6 or can be actively, for example electrically coolable.

Figure 4:
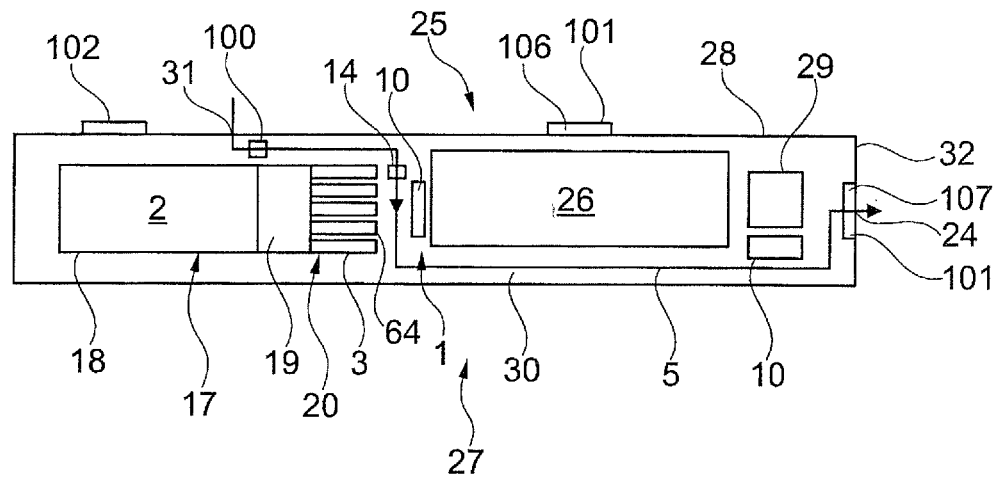
FIG. 4 is a schematic representation of an inhaler.

FIG. 4 schematically shows an inhaler 27. The inhaler 27, here an electronic cigarette product, comprises a housing 28 in which an air duct 30 is provided between at least one air inlet opening 31 and an air outlet opening 24 at a mouth end 32 of the cigarette product 27. The mouth end 32 of the cigarette product 27 thereby defines the end at which the consumer draws on the cigarette product 27 for the purpose of inhalation, thereby applying a vacuum to the cigarette product 27 and generating an air flow 5 in the air duct 30.

Advantageously, the cigarette product 27 consists of a base part 25 and a consumption unit 17, comprising the evaporator unit 20 with the evaporator 3 and the liquid reservoir 18 and is designed in particular in the form of a replaceable cartridge.

Preferably a reheating device 10 is provided in the inhaler 27. The reheating device 10 is arranged at least in part in the consumption unit 17. The reheating device 10 may also be arranged at least in part in the base part 25. The air sucked in through the inlet opening 31 is conducted in the air duct 30 to or along at least one evaporator unit 20, the evaporator unit comprising at least one evaporator 3, 3a, 3b, 3c, 3d. The example shown in FIG. 4 advantageously comprises an arrangement 1 according to one of the embodiments shown in FIGS. 1 to 3.

The evaporator unit 20 in FIG. 4 is connected or connectable to at least one liquid reservoir 18 in which at least one liquid 2 is stored. The evaporator unit 20 evaporates liquid 2 supplied to it from the liquid reservoir 18 and adds the evaporated liquid as aerosol/vapour to the air flow 5 at an outlet side 64. An advantageous volume of the liquid reservoir 18 is in the range between 0.1 ml and 5 ml, preferably between 0.5 ml and 3 ml, more preferably between 0.7 ml and 2 ml or 1.5 ml. The liquid 2 to be dosed which is stored in the liquid reservoir 18 is, for example, a mixture of 1,2-propylene glycol, glycerol, water, at least one flavour (flavouring substance) and/or at least one active ingredient, in particular nicotine and/or a medicinal active ingredient.

The electronic cigarette 27 further comprises an electric energy storage device 26 and an electronic control device 29. The energy storage device 26 is usually arranged in the base part 25 and can in particular be a disposable electrochemical battery or a rechargeable electrochemical battery, for example a lithium ion battery. The electronic control device 29 comprises at least one digital data processing device, in particular a microprocessor and/or microcontroller, in the base part 25 (as shown in FIG. 4) and/or in the consumption unit 17.

The consumption unit or cartridge 17 advantageously comprises a non-volatile data memory for storing information and/or parameters relating to the consumption unit or cartridge 17. The data memory may be part of the electronic control device 29. The data memory advantageously stores information on the composition of the liquid stored in the liquid reservoir 18, information on the process profile, in particular power/temperature control; data for state monitoring or system testing, for example leakage testing; data relating to copy protection and counterfeit protection, an ID for unique identification of the consumption unit or cartridge 17, serial number, date of manufacture and/or expiry date, and/or number of draws (number of inhalation draws by the consumer) or the time of use. The data memory is advantageously connected or connectable to the control device 29 via contacts and/or conduits.

The inhaler 27 advantageously comprises a sensor, for example a pressure or flow sensor or a flow rate measuring arrangement 100, or a pressure or flow switch, wherein in particular the control device 29 is able to determine on the basis of a sensor signal output by the sensor or switch, that a consumer is drawing at the mouth end 32 of the cigarette product 27 in order to inhale. In this case, the control device 29 controls the evaporator unit 20 to add liquid 2 from the liquid reservoir 18 as aerosol/vapour 6 to the air flow 5.

At least one actuating member 101 is advantageously provided at the housing 28, see FIG. 4. The actuating member 101 can, for example, be one or more switches, buttons, finger pressure gauges. In particular, electronic and/or capacitive actuating members 101 are conceivable. The actuating member 101 can, for example, be adapted for dosing the flavouring substances and/or active ingredients, in particular nicotine, and/or for adjusting the draw resistance.

The actuating member 101 is advantageously adapted and arranged in such a way that it can be actuated by consumers by means of finger pressure and/or mouth pressure. The actuating member 101 is advantageously designed as a finger pressure sensitive sensor 106 and/or mouth pressure sensitive sensor 107. As a finger pressure sensor or pressure sensor 106, the actuating member 101 is advantageously arranged on a tube extending between the mouth end 32 and a distal end of the housing 28, and as a mouth-pressure sensitive sensor or mouth-pressure sensor 107, the actuating member 101 is advantageously arranged on the mouth end 32 of the housing 28 for detecting the tactile contact of the consumer's lips.

The measurement of the draw strength or the suction pressure can advantageously allow the switching of bypasses 109 or other air ducts (not shown in the embodiment) and/or the adjustment of choke valves 14 or orifices in one or more air ducts 30.

The consumer or user can advantageously control the development of steam or the air flow 5 with the aerosol 6, in particular the mass flow and/or the temperature, in an intuitive manner. The evaporation quantity is advantageously adjustable by the actuating member 101 with a force sensor 106 in the grip area of the inhaler 27 to measure the contact force of the fingers. The advantage is that the evaporator capacity P of evaporator 3, whose vapour rate is variable, is adjustable to the grip strength by means of a time-resolved measurement of the actuation or grip strength of actuating element 101. Preferably, the duty cycle and/or the temperature of the evaporator 3 are adjustable in order to adjust the flavouring substances and/or active ingredients content, in particular the nicotine content, in the aerosol 6 or in the vapour phase to the grip strength by means of the time-resolved measurement of the actuating member 101.

The evaporation quantity and/or the flavouring substances and/or active ingredients content, for example the nicotine content, are advantageously controllable by the user via a plurality of independent, preferably intuitive, methods, in particular the determination of the suction pressure with the flow rate measuring arrangement 100 and the actuation of the actuating member 101. The flow rate measuring arrangement 100 or the pressure or flow sensor can be provided as an input member for the electronic control device 29.

Preferably, the electronic control device 29 is adapted to be able to advantageously adjust the duty cycle and/or the temperature of the evaporator 3 fast enough in order to be able to adjust the flavouring substances and/or active ingredients content, in particular the nicotine content, in the aerosol 6 or in the vapour phase, and the vapour rate or the mass flow, advantageously fast enough, i.e. during a draw, and independently of one another, and/or in order to be able to react advantageously fast enough to a time-resolved measurement of the measuring arrangement 100 and/or the operating element 101.

Figure 2:
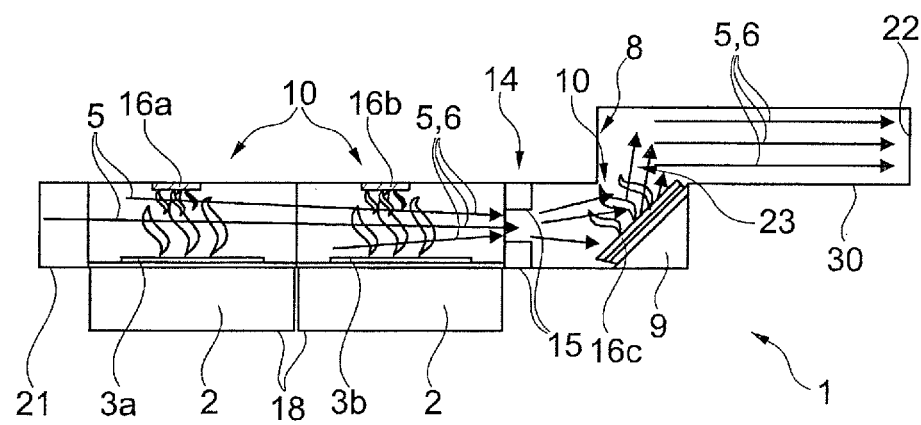
FIG. 2 is a section through an arrangement having a plurality of reheating devices.
Figure 3:
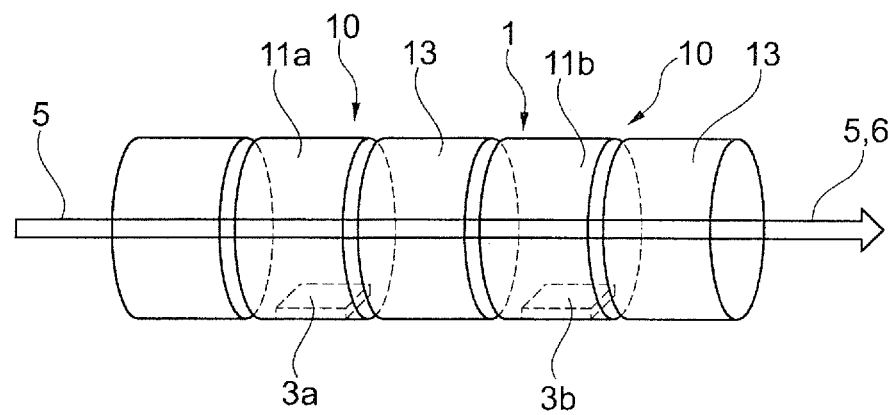
FIG. 3 is a perspective view of an arrangement having annular heat conducting elements.
Figure 6:
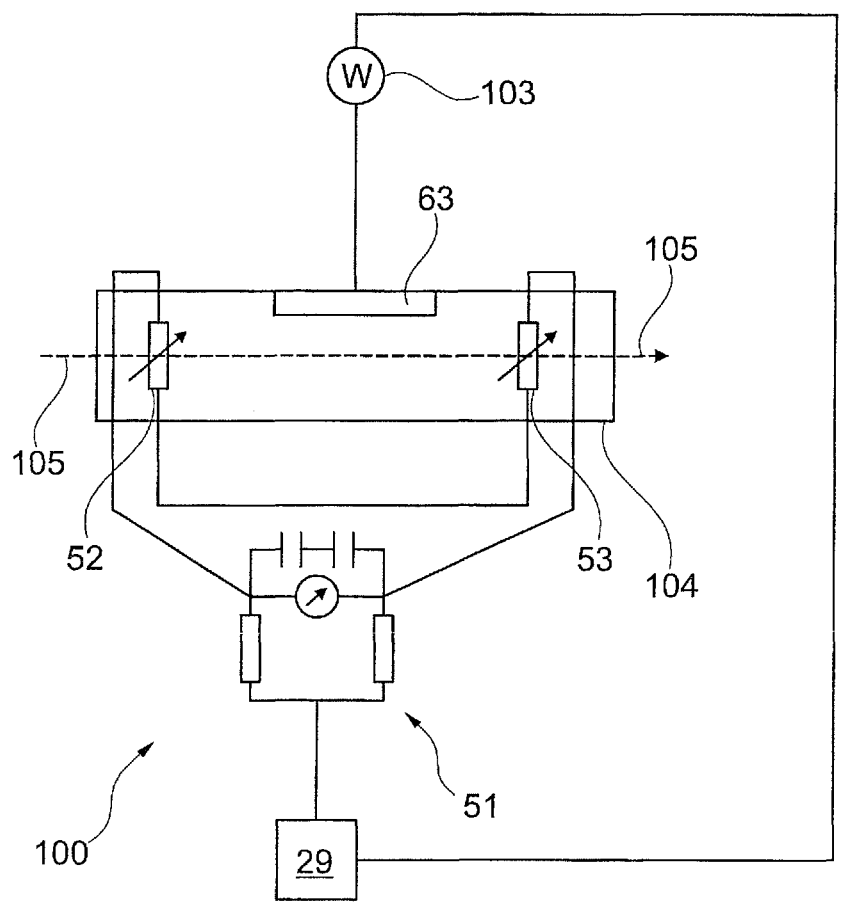
FIG. 6 is a schematic representation of a measuring arrangement for flow measurement.

A plurality of reheating devices 10 are advantageously arranged along the air duct 30, for example according to one of FIGS. 1 to 3, and/or the measuring arrangement 100, for example according to FIG. 6. The reheating devices 10 are advantageously connected to the control device 29.

In the air duct 30, said choke valve 14, air control blades 23 and/or orifices may be adjustable to change flow conditions at the evaporator 3 and/or to switch on or off a measuring duct and/or bypasses or auxiliary air ducts.

In other embodiments, a plurality of evaporator units 20 and/or evaporators 3, 3a, 3b, 3c, 3d may be provided in the air duct 30 or plurality of air ducts.

A plurality of air flows 5 is advantageously guided through a plurality of air ducts 30, each of the air ducts 30 being activatable or openable and deactivatable or closeable by a choke valve 14 or orifice. This means that an air flow 5 can be guided through an active or open-air duct 30 and an inactive or closed air duct 30 cannot be passed by an air flow 5. Each evaporator unit 20 and/or each evaporator 3, 3a, 3b, 3c, 3d is arranged such that aerosol 6 can be added to at least one of the air ducts 30. For inhalation by the consumer, the sum of all air flows 5 flowing through the air ducts 30 is directed to the mouth end 32.

In a further embodiment, it is possible by duct-wise control of the evaporators 3, 3a, 3b, 3c, 3d and/or evaporator unit 20 that the evaporators 3, 3a, 3b, 3c, 3d can start and/or stop the evaporation quickly, for example in less than 1 s, preferably less than 0.2 s, in order to be able to react suitably to the draw of the consumer and/or another control or to allow a direct reaction to the user's wish. By preferably controlling the evaporators or the evaporator 3, 3a, 3b, 3c, 3d duct by duct, the evaporation rate or the mass flow can be adjusted with an advantageously low response delay for the change of the evaporation characteristics. The response delay depends on the design of the evaporators 3, 3a, 3b, 3c, 3d, in particular the choice of material, geometry and thermal coupling to the environment, wherein micromechanical systems are advantageous due to their low heat capacity and their preferably high thermal conductivity.

A user-controlled adaptation of the air flow 5, in particular the mass flow, the flavouring substances and/or active ingredients and/or the temperature are made possible by a fast reaction time of the evaporator 3. The evaporation is advantageously adjustable with an adjustment of the evaporator temperature, the number of activated or controlled areas of the evaporator unit 20 or the evaporator(s) 3, 3a, 3b, 3c, 3d, an adjustment of the duty cycle with pulsed control and/or a combination thereof. By way of a suitable combination of the capacity P of the evaporators 3, 3a, 3b, 3c, 3d, optionally the capacity P of the reheating device 10, of the mass flow, of the temperature differences ΔT upstream and downstream of the evaporator 3, 3a, 3b, 3c, 3d and/or optionally of the temperature differences ΔT upstream and downstream of the reheating device 10, the amount of steam and the flavouring substances and/or active ingredients content, in particular the nicotine content, can be varied or are variable independently of one another.

A display device 102 is advantageously provided at the housing 28, which may, for example, comprise one or more LEDs, displays of organic light-emitting diodes (OLEDs) and/or liquid crystal displays (LC displays). Advantageously, the display device 102 may display the settings, in particular the steam quantity, temperature and/or the flavouring substances and/or active ingredients content.

In FIG. 5 an evaporator unit 20 is shown. The evaporator unit 20 comprises a block-shaped, preferably monolithic radiator or evaporator 3 made of an electrically conductive material, preferably doped silicon, doped ceramic, metal-ceramic, filter ceramic, semiconductor, in particular germanium, graphite, semi-metal and/or metal. It is not necessary that the entire evaporator 3 consists of an electrically conductive material. For example, it may be sufficient for the surface of the evaporator 3 to be coated with an electrically conductive material such as metal. In this case, the entire surface does not have to be coated, for example conductive tracks can be provided on a non-conductive base body.

The evaporator 3 is provided with a plurality of microducts 62 which connect an inlet side 61 of the evaporator 3 with an outlet side 64 in a liquid-conducting manner. The inlet side 61 is connected to the liquid reservoir 18 via a wick structure 19 in a liquid-conducting manner. The wick structure 19 is used for the passive transport of liquid from a liquid reservoir 18 to the evaporator 3 by means of capillary forces. In the contact area 61 to the evaporator 3, the wick structure 19 serves to distribute liquid evenly, to be temperature-resistant and to form a type of check valve with its relatively small pores and/or thin capillaries in order to prevent unwanted backflow of bubble-containing liquid from the evaporator 3 into the wick structure 19 and/or into the liquid reservoir 18.

The mean diameter of the microducts 62 is preferably in the range between 5 μm and 200 μm, more preferably in the range between 30 μm and 150 μm, even more preferably in the range between 50 μm and 100 μm. Due to these dimensions, a capillary effect is advantageously generated so that liquid penetrating into a microduct 62 at said inlet side 61 rises upwards through said microduct 62 until said microduct 62 is filled with liquid. The volume ratio of microducts 62 to evaporator 3, which can be described as the porosity of evaporator 3, is, for example, in the range between 10% and 50%, advantageously in the range between 15% and 40%, even more advantageously in the range between 20% and 30%, and is, for example, 25%.

The edge lengths of the surfaces of the evaporator 3 provided with microducts 62 are, for example, in the range between 0.5 mm and 3 mm, preferably between 0.5 mm and 1 mm. The dimensions of the surfaces of the evaporator 3 provided with microducts 62, for example, can be as follows: 0.95 mm×1.75 mm or 1.9 mm×1.75 mm or 1.9 mm×0.75 mm. The edge lengths of the evaporator 3, for example, can be in the range between 0.5 mm and 5 mm, preferably in the range between 0.75 mm and 4 mm, more preferably in the range between 1 mm and 3 mm. The area of the evaporator 3 (chip size) can, for example, be 1 mm×3 mm, 2 mm×2 mm or 2 mm×3 mm.

The width b of the evaporator 3 (see FIG. 5) is preferably in the range between 1 mm and 5 mm, more preferably in the range between 2 mm and 4 mm, and is for example 3 mm. The height h of the evaporator 3 (see FIG. 5) is preferably in the range between 0.05 mm and 1 mm, more preferably in the range between 0.1 mm and 0.75 mm, even more preferably in the range between 0.2 mm and 0.5 mm and is, for example, 0.3 mm.

The number of microducts 62 is preferably in the range between four and 1000. In this way, the heat input into the microducts 62 can be optimised and a secured high evaporation capacity as well as a sufficiently large steam outlet area can be realised.

The microducts 62 are arranged in the form of a square, rectangular, polygonal, round, oval or differently shaped array. The array can be in the form of a matrix with s columns and z rows, where s is advantageously in the range between 2 and 50 and more advantageously in the range between 3 and 30 and/or z is advantageously in the range between 2 and 50 and more advantageously in the range between 3 and 30. In this way, an effective and easily producible arrangement of the microducts 62 with secured high evaporation capacity can be achieved.

The cross section of the microducts 62 can be square, rectangular, polygonal, round, oval or otherwise shaped, and/or can change portion-wise in the longitudinal direction, in particular increase, decrease or remain constant.

The length of one or each microduct 62 is preferably in the range between 100 μm and 1000 μm, more preferably in the range between 150 μm and 750 μm, more preferably in the range between 180 μm and 500 μm and is, for example, 300 μm. In this way, optimum liquid absorption and portion formation can be achieved with sufficiently good heat input from the evaporator 3 into the microducts 62.

The distance between two microducts 62 is preferably at least 1.3 times the internal diameter of a microduct 62, wherein the distance is related to the centre axes of the two microducts 62. The distance can preferably be 1.5 to 5 times the internal diameter of a microduct 62, or 2 to 4 times the internal diameter of a microduct 62. In this way, optimum heat input into the microducts and a sufficiently stable arrangement and wall thickness of the microducts can be achieved.

The evaporator unit 20 has a heating voltage source 71 which is preferably controllable by the control device 29 and which is connected to the evaporator 3 via electrodes 72 on opposite sides of the evaporator 3, so that an electrical voltage Uh generated by the heating voltage source 71 leads to a current flow through the evaporator 3. Due to the ohmic resistance of the electrically conductive evaporator 3, the current flow leads to heating of the evaporator 3 and therefore to evaporation of liquid contained in the microducts 62. The vapour/aerosol 6 generated in this way escapes from the microducts 62 to the outlet side 64 and is mixed with the air flow 5, see FIG. 4. More precisely, when an air flow 5 caused by the consumer's draw through the air duct 30 is detected, the control device 29 controls the heating voltage source 71, wherein the liquid in the microducts 62 is driven out of the microducts 62 in the form of vapour/aerosol 6 by spontaneous heating.

The duration of the individual evaporation steps at different temperatures and/or an evaporation of the individual components of the individual portions of the liquid can be kept so short and/or clocked with a control frequency that the step-by-step evaporation cannot be perceived by a consumer and nevertheless a largely homogeneous, taste-conforming, repeatable precise aerosol formation can be ensured. In particular, advantageously, first, evaporation of a more readily boiling component of the liquid takes place in a first evaporation interval at a first temperature A and subsequently, evaporation of a less readily boiling component of the liquid takes place in a second evaporation interval at a second temperature B exceeding temperature A. The temperature has an influence on the adaptation of the flavouring substances and/or active ingredients provided by the consumer, since the different liquid components have different vapour pressures and their relative ratio in the vapour phase depends on the temperature.

A voltage curve Uh(t) adapted to the liquid mixture used is preferably stored in the data memory of the inhaler 27. This makes it possible to set the voltage curve Uh(t) adapted to the liquid used, so that the heating temperature of the evaporator 3, and thus also the temperature of the capillary microducts 62, can be controlled over time during the evaporation process according to the known evaporation kinetics of the respective liquid, wherein optimum evaporation results are achievable. The evaporation temperature is preferably in the range between 100° C. and 400° C., more preferably between 150° C. and 350° C., even more preferably between 190° C. and 290° C.

On the inlet side 61 of evaporator 3, a porous and/or capillary, liquid-conducting wick structure 19 is advantageously arranged. The wick structure 19 contacts the inlet side 61 of the evaporator 3 in a planar manner and covers all the microducts 62 on the inlet side, as shown in FIG. 5. On the side opposite of the evaporator 3, the wick structure is connected to the liquid reservoir 18 in a liquid-conducting manner. The direct connection of the liquid storage tank 18 to the wick structure 19 shown in FIGS. 4 and 5 is only to be understood as an example. In particular, a liquid interface and/or several liquid conduits may be provided between the liquid reservoir 18 and the wick structure 19. The liquid reservoir 18 can therefore also be arranged at a distance from the wick structure 19. The dimensions of the liquid reservoir 18 can be larger than the wick structure 19. The wick structure 19 can, for example, be inserted into an opening in a housing of the liquid reservoir 18. A plurality of evaporator units 20 may also be associated with a liquid reservoir 18. The wick structure 19 can generally be a one-piece- or multi-piece-structure.

The wick structure 19 consists of porous and/or capillary material which, due to capillary forces, is able to passively convey sufficient amounts of liquid evaporated by the evaporator 3 from the liquid reservoir 18 to the evaporator 3 in order to prevent the microducts 62 from running empty as well as problems that arise as a result.

The wick structure 19 advantageously consists of a non-conductive material in order to avoid an undesired heating of liquid in the wick structure 19 by current flow. If the wick structure 19 consists of a conductive material, which is not excluded, an insulating layer of an electrically and/or thermally insulating material, such as glass, ceramic or plastic, with through-holes corresponding to the microducts 62 and extending through the insulating layer, is advantageously provided between the wick structure 19 and the evaporator 3.

The wick structure 19 advantageously consists of one or more of the following materials: cotton, cellulose, acetate, glass fibre fabric, glass fibre ceramic, sintered ceramic, ceramic paper, aluminosilicate paper, metal foam, metal sponge, another heat-resistant, porous and/or capillary material having a suitable feed rate, or a combination of two or more of the above materials. In an advantageous practical embodiment, the wick structure 19 may comprise at least one ceramic fibre paper and/or one porous ceramic. The volume of the wick structure 19 is preferably in the range between 1 mm$^3$ and 10 mm$^3$, more preferably in the range between 2 mm³ and 8 mm³, even more preferably in the range between 3 mm³ and 7 mm³ and is, for example, 5 mm³.

The evaporator 3 can advantageously be produced from sections of a wafer with thin film technology, which has a layer thickness of preferably less than or equal to 1000 μm, more preferably less than or equal to 750 μm, even more preferably less than or equal to 500 μm. Surfaces of the evaporator 3 may advantageously be hydrophilic. The inlet side 61 and/or the outlet side 64 of the evaporator 3 can be advantageously microstructured or have microgrooves.

The evaporator unit 20 is adjusted in such a way that a quantity of liquid is added preferably in the range between 1 μl and 20 μl, more preferably between 2 μl and 10 μl, even more preferably between 3 μl and 5 μl, typically 4 μl per consumer's draw. Preferably the evaporator unit 20 may be adjustable with regard to the liquid/vapour quantity per draw.

The inhaler 27 advantageously comprises a flow rate measuring arrangement 100 for measuring the air volume flow flowing through the inhaler.

An advantageous flow rate measuring arrangement 100 is described below with reference to FIG. 6. The measuring arrangement 100 or the flow rate measuring arrangement in accordance with FIG. 6 measures the flow rate of the air flow 5 or a measuring air flow 105 through the air duct 30 or a measuring air duct 104 on a thermal basis or according to the heating principle, the air flow 5 being heated by a temperature difference ΔT by means of a heating device 63.

The heating device 63 can, for example, be formed by an evaporator 3 or a reheating device 10. In the process, the thermal behaviour of the evaporator 3 and/or of the reheating device 10, in particular of a silicon heating device, is used. The measuring method according to the heating principle can therefore be combined with the reheating of the air flow 5 by means of the reheating device 10. Advantageously, the heating device 63 is provided in addition to and independent of the evaporator 3 and the reheating devices 10 allowing for a more accurate flow measurement.

The air flow 5 flowing through the air duct 3 passes through a plurality of temperature sensors 52, 53 to measure the temperature of the air passing through each respective temperature sensor 52, 53. The temperature sensors 52, 53 are spaced from each other in the direction of the flow, i.e. are arranged sequentially. An upstream temperature sensor 52 is connected in front of the heating device 63, i.e. upstream of the heating device 63. A downstream temperature, sensor 53 is connected after the heating device 63, i.e. downstream of the heating device 63. The temperature sensors 52, 53 output measuring temperature signals to an evaluation circuit 51 and/or the electronic control device 29 of the inhaler 27.

The example in FIG. 6 shows an evaluation circuit 51 for determining the temperature difference ΔT between the temperatures measured with the temperature sensors 52, 53. This evaluation can of course also be carried out in the electronic control device 29, so that a separate evaluation circuit 51 may be dispensable.

The heating device 63 heats up the air flow 5 in the air duct 30 with an electrical heating power P. The measuring arrangement or flow rate measuring arrangement 100 preferably comprises a wattmeter 103 for measuring the power P generated by the heating device 103 and delivered to the air flow 5. The wattmeter 103 may be a separate circuit. Alternatively, the heating power may be known from an electronic control unit for the heating device 63 and be transmitted to the electronic control unit 29. The wattmeter 103 may thus be implemented in an electronic control unit for the heating device 63 and/or in the electronic control device 29.

The heat supplied to the air flow 5 increases its temperature. The upstream temperature sensor 52 is used to measure the temperature of the air flow 5 upstream of the evaporator 3 or in the air flow 5 prior to the heating procedure by the heating device 63. The downstream temperature sensor 53 is used to measure the temperature of the air flow 5 downstream of the heating device 63 or in the air flow 5 after the heating procedure by the heating device 63.

The electronic control device 29 determines the mass flow $\Delta m/\Delta t$ of the air flow 5 flowing through the air duct 30 by means of the equation $\Delta m/\Delta t = P/(c \cdot \Delta T)$, wherein P is the heating power measured with the wattmeter 103, $\Delta T$ is the temperature difference, in particular between the temperature sensors 52, 53 and c is the known heat capacity of the air or of the air/aerosol mixture. The volume flow of the air flow 5 through the air duct 30 is related to the mass flow by means of a known function or a proportionality constant, which for example is determinable by calibration and storable in the electronic control device 29, and is easily determinable by the electronic control device 29 if required.

Figure 7:
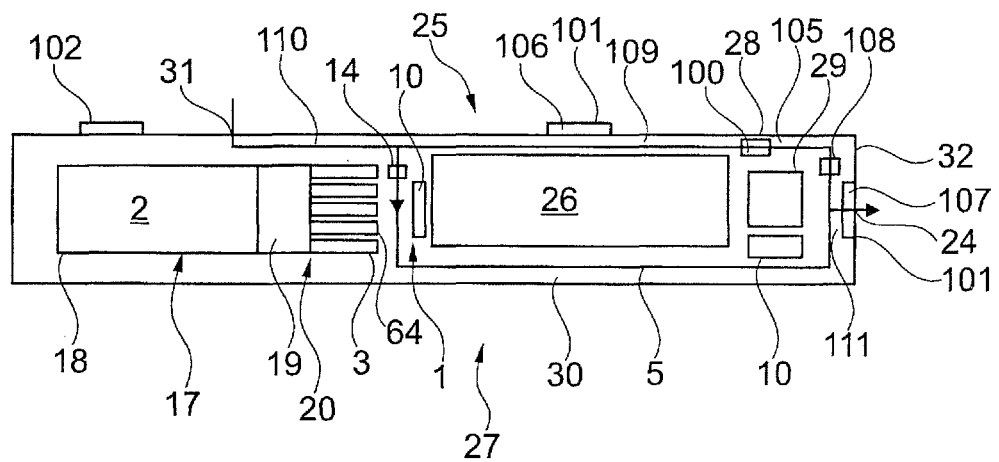
FIG. 7 is a schematic representation of an inhaler.

Preferably both temperature sensors 52, 53 and the heating device 63 of the flow rate measuring arrangement 100 are arranged in front of the first evaporator 3 or in a measuring duct 104 provided as bypass 109, as shown for example in FIG. 4 or FIG. 7. In these cases, the constant heat capacity of air without steam or aerosol can be used as heat capacity c, which increases the accuracy of the measurement. However, it is also conceivable that the flow rate measuring arrangement 100 is arranged fully or in part behind the first evaporator 3. This is particularly the case if the heating device 63 is formed by an evaporator 3 and/or a reheating device 10. In this case, the heat capacity c is assumed to be the heat capacity of the air/vapour/aerosol mixture.

Preferably, the flow rate measuring arrangement 100 is set up for time-resolved measurement of the draw strength by the user. The evaporator capacity of evaporator 3, whose vapour rate is variable, is particularly preferred and is adaptable to the draw strength of the consumer on the basis of the time-resolved measurement. Particularly advantageously, the duty cycle and/or the temperature of the evaporator 3 are adjustable in order to adjust the flavouring substances and/or active ingredients content, in particular the nicotine content, in the aerosol 6 or in the vapour phase to the draw strength by means of the time-resolved measurement of the measuring arrangement 100.

The flow rate measuring arrangement 100 may be advantageously used to activate the inhaler 27, for example by activating the inhaler 27 when the consumer blows in order to detect an error-free detection of the activation by the consumer. The control device 29 may convert the consumer's blowing into a control signal, for example for the evaporator unit 20, in order to adjust a predetermined amount of steam, for example by means of a certain way of blowing.

Preferably, the inhaler 27 may only be adjustable, controllable or regulatable by the user's blowing and/or drawing as measured by the flow rate measuring arrangement 100 or pressure or flow sensors, so that switches, buttons or the like are unnecessary. By way of example, long blowing may mean calling up a setting menu, wherein by means of short blowing and/or short drawing one or more settings may be changed. For example, the setting may be completed by another long blow and/or after a defined time. Advantageously, the evaporation quantity is therefore controllable or regulatable by the draw resistance or by the suction pressure applied by the consumer.

FIG. 7 shows an inhaler 27, which is explained with regard to the differences from the embodiment shown in FIG. 4. The inhaler 27 shown in FIG. 7 comprises a bypass duct or secondary air duct 109. The flow rate measuring arrangement 100 (i.e. the downstream temperature sensor 53, possibly the upstream temperature sensor 52 and/or the heating device 63) is advantageously arranged in the bypass duct or secondary air duct 109 without the evaporator 3. Similar to the arrangement shown in FIG. 4, this has the advantage that the flow measurement is not influenced by the vapour/aerosol content in the air flow 5 or the measuring air flow 105.

The bypass duct 109 is a duct which is different at least in part from the air duct 30. Advantageously, upstream of the evaporator 3 or between the inlet port 31 and the evaporator 3 a bifurcation 110 is provided, at which the bypass duct 109 and the air duct 30 separate. The bypass duct 109 and the air duct 30 extend parallel to one another up to a node 111, at which they advantageously form a common air flow which is guided to the air outlet opening 24 and in particular may be inhaled by the consumer. The bypass duct 109 is advantageously used to bypass the evaporator unit 20 or the evaporator 3.

The bypass duct 109 may advantageously comprise an orifice 108 or a valve, the orifice 108 being adapted to close or open the bypass duct 109, i.e. to make the bypass duct 109 passable or impassable for an air flow. This allows, for example, the flow conditions at the at least one evaporator to be regulated and/or the flow resistance in the inhaler 27 to be influenced.

In an embodiment (not shown), a choke valve 14, as explained in the description for FIG. 1, is arranged in the bypass duct 109 to regulate/control the flow resistance in the bypass duct.

In the embodiment shown in FIG. 7, the bypass duct 109 forms the measuring duct 104 shown in FIG. 6, which guides the measuring air flow 105 to the flow measurement with the flow rate measuring arrangement 100.

Figure 8:
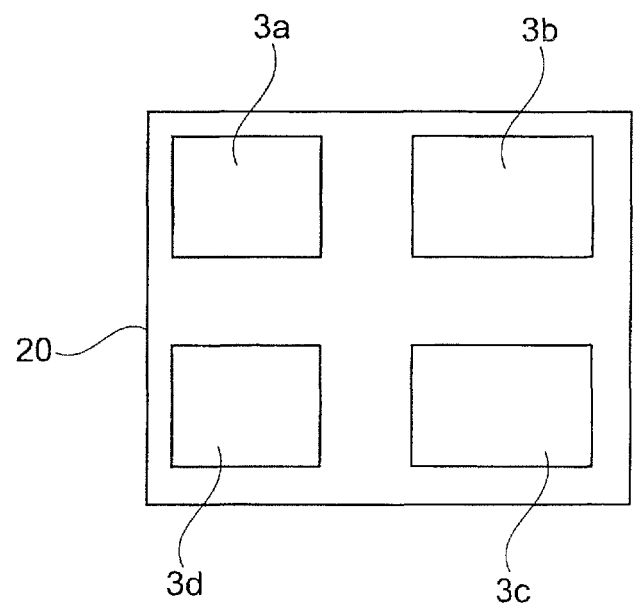
FIG. 8 is a schematic representation of an evaporator unit.

FIG. 8 shows a multi-duct evaporator unit 20 having a plurality of, herein four, evaporators 3a, 3b, 3c, 3d. Advantageously, the evaporators 3a, 3b, 3c, 3d may be heated or controlled separately from each other, which allows a fast reaction time of the evaporation capacity of the evaporator unit 20. The evaporators 3a, 3b, 3c, 3d may be connected and/or connectable to one or more liquid storage tanks 18. Thus, for example, two of the evaporators 3a, 3b, 3c, 3d may evaporate and add to the air flow 5 different liquids 2 with different flavouring substances and/or active ingredients.

Individual evaporators 3a, 3b, 3c, 3d (FIG. 8), alternatively individual evaporator chips and/or areas of an evaporator 3, may advantageously be controlled separately from one another, in particular switched on and off, i.e. activated. Thus, the steam quantity or mass flow may be adjusted or regulated by the control pulses and/or with the constellation of the controlled evaporators 3a, 3b, 3c, 3d or regions of an evaporator 3. For example, a gradation may be provided for regulating the control of evaporator 3 or regions of an evaporator 3 where different modes are conceivable. For example, for a weak or for little evaporation two evaporators 3a, 3b, for a standard or an average quantity three evaporators 3a, 3b, 3c and for a strong or a lot of evaporation four evaporators 3a, 3b, 3c, 3d, or alternatively regions of one evaporator 3, may be activatable.

EMBODIMENTS

Embodiment 1

Arrangement (1) for an inhaler (27) comprising:
at least one electric evaporator (3, 3a, 3b, 3c, 3d) for evaporating liquid (2) supplied from the evaporator (3, 3a, 3b, 3c, 3d) and for adding the evaporated liquid (2) to an air flow (5) flowing through the inhaler (27) to form an aerosol (6), and
a flow rate measuring arrangement (100) for measuring the volume and/or mass flow of the air flow (5) flowing through the inhaler (27),
characterised in that
the flow rate measuring arrangement (100) comprises a heating device (63), a downstream temperature sensor (53) arranged downstream of the heating device (63) for measuring an air outlet temperature, and an electronic control device (29), and
the electronic control device (29) is adapted to determine the volume and/or mass flow of the air flow (5) flowing through the inhaler (27) on the basis of a temperature difference between the air outlet temperature and an air inlet temperature of the air flow (5) upstream of the heating device (63).

Embodiment 2

Arrangement (1) according to embodiment 1, characterised in that
the flow rate measuring arrangement (100) comprises an upstream temperature sensor (52) arranged upstream of the heating device (63) for measuring the air inlet temperature of the air flow (5).

Embodiment 3

Arrangement (1) according to any of the preceding embodiments, characterised in that
the heating device (63) is arranged upstream of the evaporator or the evaporators (3, 3a, 3b, 3c, 3d) of the inhaler (27).

Embodiment 4

The Arrangement (1) according to any of the preceding embodiments, characterised in that
the heating device (63) is formed by one of the evaporators (3, 3a, 3b, 3c, 3d).

Embodiment 5

Arrangement (1), preferably according to any of the preceding embodiments, comprising at least one electric evaporator (3, 3a, 3b, 3c, 3d) for evaporating liquid (2) supplied from the evaporator (3, 3a, 3b, 3c, 3d) and for adding the evaporated liquid (2) to an air flow (5) flowing through the inhaler (27) to form an aerosol (6), characterised in that
the arrangement (1) comprises a reheating device (10) for reheating the aerosol (6).

Embodiment 6

Arrangement according to embodiment 5, characterised in that
the heating device (63) is formed by the reheating device (10).

Embodiment 7

Arrangement (1) according to any of the preceding embodiments, characterised in that
the electronic control device (29) is adapted to determine the volume and/or mass flow of the air flow (5) flowing through the inhaler (27) by applying the equation $\Delta m/\Delta t = P/(c \cdot \Delta T)$, wherein $\Delta m/\Delta t$ is the mass flow, P is the heating power of the heating device (63), $\Delta T$ is the temperature difference between the air outlet temperature and the air inlet temperature and c is the heat capacity of the air heated by the heating device (63).

Embodiment 8

Arrangement (1) according to any of the preceding embodiments, characterised in that
the arrangement (1) comprises a wattmeter (103) for determining the heating power P of the heating device (63).

Embodiment 9

Arrangement (1) according to any of the preceding embodiments, characterised in that
the electronic control device (29) is adapted to control the at least one evaporator (3, 3a, 3b, 3c, 3d) as a function of the measured flow rate of the air flow (5) through the inhaler (27).

Embodiment 10

Arrangement (1) according to any of the preceding embodiments, characterised in that
the evaporator (3, 3a, 3b, 3c, 3d) is controllable on the basis of a signal from an actuating member (101).

Embodiment 11

Arrangement (1) according to any of the preceding embodiments, characterised in that
at least the heating device (63) and the downstream temperature sensor (53) are arranged in a measuring duct (104).

Embodiment 12

Arrangement (1) according to any of the preceding embodiments, characterised in that
the at least one electric evaporator (3, 3a, 3b, 3c, 3d) is a multi-duct, in particular a temperature-controlled evaporator (3, 3a, 3b, 3c, 3d).

Embodiment 13

Arrangement (1) according to any of the preceding embodiments, characterised in that
the evaporation quantity of the evaporated liquid (2) is adjustable, controllable and/or regulatable.

Embodiment 14

Arrangement (1) according to any of the preceding embodiments, characterised in that
the nicotine quantity of the evaporated liquid (2) is adjustable, controllable and/or regulatable.

Embodiment 15

Arrangement (1) according to any of the preceding embodiments, characterised in that
the temperature of the evaporator (3, 3a, 3b, 3c, 3d) is adjustable, controllable and/or regulatable.

Embodiment 16

Arrangement (1) according to any of the preceding embodiments, characterised in that
the number of activated evaporators (3, 3a, 3b, 3c, 3d) and/or evaporator regions is adjustable, controllable and/or regulatable.

Embodiment 17

Arrangement (1) according to any of the preceding embodiments, characterised in that
the duty cycle of the evaporator (3, 3a, 3b, 3c, 3d) is adjustable, controllable and/or regulatable.

Embodiment 18

Arrangement (1) according to any of the preceding embodiments, characterised in that
the arrangement (1) has a force sensor (106, 107) for measuring the finger pressing force or the mouth pressing force by the consumer.

Embodiment 19

Arrangement (1) according to any of the preceding embodiments, characterised in that
the flow rate measuring arrangement (100) is usable as an input element for inputting information into the electronic control device (29) by the consumer.

Embodiment 20

Arrangement (1) according to embodiment 19, characterised in that
the flow rate measuring arrangement (100) is adapted for detecting blowing into or drawing out of the inhaler (27) by the consumer as input.

Embodiment 21

Arrangement (1) according to one of the embodiments 19 or 20, characterised in that
the flow rate measuring arrangement (100) is usable for activating the inhaler (27).

Embodiment 22

Arrangement (1) according to any of embodiments 19 to 21, characterised in that
the flow rate measuring arrangement (100) is usable for steam quantity adjustment by the consumer.

Embodiment 23

Arrangement (1) according to any of embodiments 19 to 22, characterised in that
an orifice (108) and/or a bypass duct (109) for regulating the flow conditions is provided on the at least one evaporator (3, 3a, 3b, 3c, 3d).

Embodiment 24

Arrangement (1) according to any of the preceding embodiments, characterised in that
the evaporator (3, 3a, 3b, 3c, 3d) is silicon-based at least in part, preferably a micro-electro-mechanical system (MEMS).

Embodiment 25

Base part for an inhaler (27) comprising an assembly (1) according to any of the preceding embodiments.

Embodiment 26

Inhaler (27) having an assembly (1) according to embodiments 1 to 24.

The invention claimed is:

1. An arrangement for an inhaler, comprising:
at least one electric evaporator for evaporating liquid supplied to the at least one electric evaporator and for adding the evaporated liquid to an air flow flowing through the inhaler to form an aerosol; and
a flow rate measuring arrangement for measuring the volume and/or mass flow of the air flow flowing through the inhaler,
wherein the flow rate measuring arrangement comprises:
a heating device;
a downstream temperature sensor arranged downstream of the heating device for measuring an air outlet temperature; and
an electronic control device,
wherein the electronic control device is configured to determine the volume and/or mass flow of the air flow flowing through the inhaler on the basis of a temperature difference between the air outlet temperature and an air inlet temperature of the air flow upstream of the heating device, and
wherein the electronic control device is configured to determine the volume and/or mass flow of the air flow flowing through the inhaler by applying the equation $\Delta m/\Delta t = P/(c \cdot \Delta T)$, where $\Delta m/\Delta t$ is the mass flow, P is the heating power of the heating device, $\Delta T$ is the temperature difference between the air outlet temperature and the air inlet temperature, and c is the heat capacity of the air heated by the heating device.

2. The arrangement according to claim 1,
wherein the flow rate measuring arrangement comprises an upstream temperature sensor arranged upstream of the heating device for measuring the air inlet temperature of the air flow.

3. The arrangement according to claim 1,
wherein the heating device is arranged upstream of one or more electric evaporators of the at least one electric evaporator.

4. The arrangement according to claim 1,
wherein the heating device is formed by one of the at least one electric evaporators.

5. The arrangement according to claim 1, further comprising:
a reheating device for reheating the aerosol.

6. The arrangement according to claim 5,
wherein the heating device is formed by the reheating device.

7. The arrangement according to claim 1, further comprising:
a wattmeter for determining the heating power P of the heating device.

8. The arrangement according to claim 1,
wherein the electronic control device is configured to control the at least one electric evaporator as a function of the measured flow rate of the air flow through the inhaler.

9. The arrangement according to claim 1,
wherein the at least one electric evaporator is controllable on the basis of a signal from an actuating member.

10. The arrangement according to claim 1,
wherein at least the heating device and the downstream temperature sensor are arranged in a measuring duct.

11. The arrangement according to claim 1,
wherein the at least one electric evaporator is a multi-duct evaporator, and a temperature-controlled evaporator.

12. The arrangement according to claim 1,
wherein an evaporation quantity of the evaporated liquid is adjustable, controllable, and/or regulatable.

13. The arrangement according to claim 1,
wherein a nicotine quantity of the evaporated liquid is adjustable, controllable and/or regulatable.

14. The arrangement according to claim 1,
wherein a corresponding at least one temperature of the at least one electric evaporator is adjustable, controllable, and/or regulatable.

15. The arrangement according to claim 1,
wherein a number of activated evaporators and/or evaporator regions of the at least one electric evaporator is adjustable, controllable and/or regulatable.

16. The arrangement according to claim 1,
wherein a duty cycle of the evaporator is adjustable, controllable, and/or regulatable.

17. The arrangement according to claim 1, further comprising:
a force sensor for measuring a finger pressing force or a mouth pressing force by a user of the inhaler.

18. The arrangement according to claim 1,
wherein the flow rate measuring arrangement is usable as an input element for inputting information into the electronic control device by a user of the inhaler.

19. The arrangement according to claim 18,
wherein the flow rate measuring arrangement is configured to detect blowing into or drawing out of the inhaler by the user of the inhaler as input.

20. The arrangement according to claim 18,
wherein the flow rate measuring arrangement is usable for activating the inhaler.

21. The arrangement according to claim 18,
wherein the flow rate measuring arrangement is usable for steam quantity adjustment by the user of the inhaler.

22. The arrangement according to claim 18,
wherein an orifice and/or a bypass duct for regulating flow conditions is provided on the at least one electric evaporator.

23. The arrangement according to claim 1,
wherein the at least one electric evaporator is silicon-based at least in part, and a micro-electro-mechanical system (MEMS).

24. A base part for an inhaler, comprising:
an arrangement for an inhaler according to claim 1.
25. An inhaler, comprising:
an arrangement for an inhaler according to claim 1.

* * * * *